United States Patent
Beschorner et al.

(10) Patent No.: US 7,626,075 B2
(45) Date of Patent: Dec. 1, 2009

(54) GROWTH OF FOREIGN CELLS IN FETAL ANIMALS FACILITATED BY CONDITIONAL AND SELECTIVE DESTRUCTION OF NATIVE HOST CELLS

(75) Inventors: William E. Beschorner, Omaha, NE (US); Carlos E. Sosa, Omaha, NE (US); Scott C. Thompson, Omaha, NE (US)

(73) Assignee: Ximerex, Inc., Blair, NE (US)

( * ) Notice: Subject to any disclaimer, the term of this patent is extended or adjusted under 35 U.S.C. 154(b) by 0 days.

(21) Appl. No.: 10/527,587

(22) PCT Filed: Sep. 17, 2003
(Under 37 CFR 1.47)

(86) PCT No.: PCT/US03/29251

§ 371 (c)(1),
(2), (4) Date: Feb. 21, 2006

(87) PCT Pub. No.: WO2004/027029

PCT Pub. Date: Apr. 1, 2004

(65) Prior Publication Data

US 2007/0134212 A1   Jun. 14, 2007

Related U.S. Application Data

(60) Provisional application No. 60/411,790, filed on Sep. 19, 2002.

(51) Int. Cl.
*A01K 67/00* (2006.01)
*C12N 5/00* (2006.01)
*C12N 5/08* (2006.01)

(52) U.S. Cl. .............. 800/8; 435/325; 435/370
(58) Field of Classification Search .......... 800/8; 435/325, 370
See application file for complete search history.

(56) References Cited

U.S. PATENT DOCUMENTS 5,672,346 A    9/1997  Srour et al.
6,017,896 A *  1/2000  Sorscher et al. ............ 514/44
6,451,571 B1 * 9/2002  Loeb et al. ................. 435/194
6,995,299 B2 * 2/2006  Wu et al. .................... 800/9

FOREIGN PATENT DOCUMENTS

WO    95/07718 A1    3/1995
WO    01/32009 A1    5/2001

OTHER PUBLICATIONS

Surbek et al. Hum. Reprod. Update 7:85-91; 2001.*
Bernstin et al.: "Variation in long-term engraftment of a large . . . ", Biol.Blood Marrow Transplant, Nov. 1997 vol. 3, No. 5, pp. 247-245, entire reference.
Wang et al.: "Primitive human hematopeietic cells are enriched . . . " Blood, Jun. 1, 1997, vol. 89, No. 11, pp. 3919-3924, entire reference.
Braun et al., "Hepatocyte transplantation in a model of toxin-induced liver disease: variable therapeutic effect during replacement of damaged parenchyma by donor cells," Nature Medicine, vol. 6, No. 3, Mar. 2000, pp. 320-326.
Beschorner et al., "Human hepatocytes from fetal pigs infused with hepatocytes or marrow," Cell Transplantation, vol. 10, No. 6, 2001, p. 531.
Beschorner et al., "Transgenic pigs expressing the suicide gene thymidine kinase in the liver," Xenotransplantation, vol. 10, No. 5, Sep. 2003, p. 530 & VII Congress of the International Xenotransplantation Association (IXA); Glasgow, Scotland, UK; Sep. 30-Oct. 4, 2003.
Beschorner et al., "Transgenic pigs producing the suicide gene thymidine kinase in the liver. Facilitation of human hepatocytes in the pig liver," Xenotransplantation, vol. 14, No. 5, Sep. 2007, p. 383 & Joint Meeting of the International-Xenotransplantation-Association/International-Pancreas-and-Islet; Minneapolis, MN, USA; Sep. 15-20, 2007.
Beschorner et al., "Selective and conditional depletion of pig cells with transgenic pigs and specific liposomes," Xenotransplantation, vol. 10, No. 5, Sep. 2003, p. 497 & VII Congress of the International Xenotransplantation Association (IXA); Glasgow, Scotland, UK; Sep. 30-Oct. 4, 2003.

* cited by examiner

*Primary Examiner*—Fereydoun G Sajjadi
(74) *Attorney, Agent, or Firm*—Banner & Witcoff, Ltd.

(57) ABSTRACT

Foreign cells can be grown in fetal non-mammalian hosts for the production of transplant organs and tissues, the development of new therapeutic agents, and the production of biological factors and drugs. Tissue-specific injury to fetal host target cells is carried without substantial injury to the maternal host or foreign cells, providing an environment in which the injured tissue can be regenerated with the foreign cells.

22 Claims, 2 Drawing Sheets

SEQUENCE LISTING

<160> NUMBER OF SEQ ID NOS: 5

<210> SEQ ID NO 1
<211> LENGTH: 224
<212> TYPE: DNA
<213> ORGANISM: Pig

<400> SEQUENCE: 1

| | |
|---|---|
| gaattgacca ggtcttgtgg agaaaacaga tccagacggc aaacatacgc aagggattta | 60 |
| gtcaaacaca tttttggcaa aaaaactatg aattttgtaa tcagttgtga gccaatgaaa | 120 |
| tacaaaaatg agtctagtta ataatctaca attattggtt aaagaagtat attagtgctg | 180 |
| actttcctct gttcgtccta ccttttcttt tctatcaacc ccac | 224 |

<210> SEQ ID NO 2
<211> LENGTH: 2241
<212> TYPE: DNA
<213> ORGANISM: Homo sapiens

<400> SEQUENCE: 2

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcc tgcagggcct gaaataacct ctgaaagagg | 240 |
| aacttggtta ggtaccttct gaggctgaaa gaaccagctg tggaatgtgt gtcagttagg | 300 |
| gtgtggaaag tccccaggct ccccagcagg cagaagtatg caaagcatgc atctcaatta | 360 |
| gtcagcaacc aggtgtggaa agtccccagg ctccccagca ggcagaagta tgcaaagcat | 420 |
| gcatctcaat tagtcagcaa ccatagtccc actgcaggaa ttgaccaggt cttgtggaga | 480 |
| aaacagatcc agacggcaaa catacgcaag ggatttagtc aaacacattt ttggcaaaaa | 540 |
| aactatgaat tttgtaatca gttgtgagcc aatgaaatac aaaaatgagt ctagttaata | 600 |
| atctacaatt attggttaaa gaagtatatt agtgctgact ttcctctgtt cgtcctacct | 660 |
| tttcttttct atcaacccca catggcctcg taccccggcc atcaacacgc gtctgcgttc | 720 |
| gaccaggctg cgcgttctcg cggccatagc aaccgacgta cggcgttgcg ccctcgccgg | 780 |
| cagcaagaag ccacggaagt ccgcccggag cagaaactgc ccacgctact gcgggtttat | 840 |
| atagacggtc cccacgggct ggggaaaacc accaccacgc aactgctggt ggccctgggt | 900 |
| tcgcgcgacg atatcgtcta cgtacccgag ccgatgactt actggcgggt gctggggggct | 960 |
| tccgagacaa tcgcgaacat ctacaccaca caacaccgcc tcgaccaggg tgagatatcg | 1020 |
| gccggggacg cggcggtggt aatgacaagc gcccagataa caatgggcat gccttatgcc | 1080 |
| gtgaccgacg ccgttctggc tcctcatatc gggggggagg ctgggagctc acatgccccg | 1140 |
| cccccggccc tcaccctcat cttcgaccgc catcccatcg ccgccctcct gtgctacccg | 1200 |
| gccgcgcggt accttatggg cagcatgacc ccccaggccg tgctggcgtt cgtggccctc | 1260 |
| atcccgccga ccttgcccgg caccaacatc gtgcttgggg ccttccggga ggacagacac | 1320 |
| atcgaccgcc tggccaaacg ccagcgcccc ggcgagcggc tggacctggc tatgctggct | 1380 |
| gcgattcgcc gcgtttacgg gctacttgcc aatacggtgc ggtatctgca gtgcggcggg | 1440 |
| tcgtggcggg aggactgggg acagcttccg gggacggccg tgccgcccca gggtgccgag | 1500 |
| ccccagagca acgcgggccc acgaccccat atcggggaca cgttatttac cctgtttcgg | 1560 |

-continued

```
gcccccgagt tgctggcccc caacggcgac ctgtataacg tgtttgcctg ggccttggac      1620
gtcttggcca aacgcctccg ttccatgcac gtctttatcc tggattacga ccaatcgccc      1680
gccggctgcc gggacgccct gctgcaactt acctccggga tggtccagac ccacgtcacc      1740 accccggct ccataccgac gatatgcgac ctggcgcgca cgtttgcccg ggagatgggg       1800
gaggctaact gagaattcgc tagctctcta gtcgagaatt cgctagctcg acatgataag      1860
atacattgat gagtttggac aaaccacaac tagaatgcag tgaaaaaaat gctttatttg      1920
tgaaatttgt gatgctattg ctttatttgt gaaatttgtg atgctattgc tttatttgta      1980
accattataa gctgcaataa acaagttaac aacaacaatt gcattcattt tatgtttcag      2040
gttcaggggg aggtgtggga ggttttttaa agcaagtaaa acctctaaga acacaggtaa      2100
gtgccgtgtg tggttcccgc gggcctggcc tctttacggg ttatggccct tgcgtgcctt      2160
gaattacttc cacctggctg cagtacgtga ttcttgatcc cgagcttcgg gttggaagtg      2220
ggtgggagag ttcgaggcct t                                                2241
```

<210> SEQ ID NO 3
<211> LENGTH: 1506
<212> TYPE: DNA
<213> ORGANISM: fungus

<400> SEQUENCE: 3

```
gacggatcgg gagatctccc gatccctat ggtcgactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcc tgcagggcct gaaataacct ctgaaagagg      240
aacttggtta ggtaccttct gaggctgaaa gaaccagctg tggaatgtgt gtcagttagg      300
gtgtggaaag tccccaggct ccccagcagg cagaagtatg caaagcatgc atctcaatta      360
gtcagcaacc aggtgtggaa agtccccagg ctccccagca ggcagaagta tgcaaagcat      420
gcatctcaat tagtcagcaa ccatagtccc actgcagttt gaggagaata tttgttatat      480
ttgcaaaata aaataagttt gcaagttttt tttttctgcc ccaagagct ctgtgtcctt      540 gaacataaaa tacaaataac cgctatgctg ttaattattg gcaaatgtcc cattttcaac      600
ctaaggaaat accataaagt aacagatata ccaacaaaag gttactagtt aacaggcatt      660
gcctgaaaag agtataaaag aatttcagca tgattttcca tattgtgctt ccaccactgc      720
caataacacc atggtgacag ggggaatggc aagcaagtgg gatcagaagg gtatggacat      780
tgcctatgag gaggcggcct taggttacaa agagggtggt gttcctattg gcggatgtct      840
tatcaataac aaagacggaa gtgttctcgg tcgtggtcac aacatgagat ttcaaaaggg      900
atccgccaca ctacatggtg agatctccac tttggaaaac tgtgggagat tagagggcaa      960
agtgtacaaa gataccactt tgtatacgac gctgtctcca tgcgacatgt gtacaggtgc     1020
catcatcatg tatggtattc cacgctgtgt tgtcggtgag aacgttaatt tcaaaagtaa     1080
gggcgagaaa tatttacaaa ctagaggtca cgaggttgtt gttgttgacg atgagaggtg     1140 taaaagatc atgaaacaat ttatcgatga agacctcag gattggtttg aagatattgg     1200
tgagtaggct agctctctag tcgagaattc gctagctcga catgataaga tacattgat      1260 agtttggaca aaccacaact agaatgcagt gaaaaaaatg ctttatttgt gaaatttgtg      1320
atgctattgc tttatttgtg aaatttgtga tgctattgct ttatttgtaa ccattataag      1380
ctgcaataaa caagttaaca acaacaattg cattcatttt atgtttcagg ttcaggggga      1440
```
ggtgtgggag gtttttttaaa gcaagtaaaa cctctacaaa tgtggtagat ccatttaaat  1500
gttaat  1506

<210> SEQ ID NO 4
<211> LENGTH: 2294
<212> TYPE: DNA
<213> ORGANISM: Cytomegalovirus

<400> SEQUENCE: 4
gacggatcgg gagatctccc gatccctat ggtcgactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggac tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgagctcgg atccactagt ccagtgtggt ggaattctgc  960
agataatggc ctcgtacccc ggccatcaac acgcgtctgc gttcgaccag gctgcgcgtt  1020
ctcgcggcca tagcaaccga cgtacggcgt tgcgccctcg ccggcagcaa gaagccacgg  1080
aagtccgccc ggagcagaaa atgcccacgc tactgcgggt ttatatagac ggtccccacg  1140
ggatggggaa aaccaccacc acgcaactgc tggtggccct gggttcgcgc gacgatatcg  1200
tctacgtacc cgagccgatg acttactggc gggtgctggg ggcttccgag acaatcgcga  1260
acatctacac cacacaacac cgcctcgacc agggtgagat atcggccggg gacgcggcgg  1320
tggtaatgac aagcgcccag ataacaatgg gcatgcctta tgccgtgacc gacgccgttc  1380
tggctcctca tatcgggggg gaggctggga gctcacatgc cccgccccg gccctcaccc  1440 tcatcttcga ccgccatccc atcgccgccc tcctgtgcta cccggccgcg cggtaccttca  1500 tgggcagcat gacccccag gccgtgctgg cgttcgtggc cctcatcccg ccgaccttgc  1560
ccggcaccaa catcgtgctt ggggcccttc cggaggacag acacatcgac cgcctggcca  1620
aacgccagcg ccccggcgag cggctggacc tggctatgct ggctgcgatt cgccgcgttt  1680
acgggctact tgccaatacg gtgcggtatc tgcagtgcgg cgggtcgtgg cgggaggact  1740
ggggacagct ttcggggacg gccgtgccgc ccagggtgc cgagcccag agcaacgcgg  1800 gcccacgacc ccatatcggg gacacgttat ttaccctgtt tcgggccccc gagttgctgg  1860
cccccaacgg cgacctgtat aacgtgtttg cctgggcctt ggacgtcttg gccaaacgcc  1920
tccgttccat gcacgtcttt atcctggatt acgaccaatc gccgccggc tgccgggacg  1980 ccctgctgca acttaccctcc gggatggtcc agacccacgt caccaccccc ggctccatac  2040

-continued

| | |
|---|---|
| cgacgatatg cgacctggcg cgcacgtttg cccgggagat gggggaggct aactgagagt | 2100 |
| agtcgccgtg aacgttcttt ttcgcaacgg gtttgccgcc agaacacagg taagtgccgt | 2160 |
| gtgtggttcc cgcgggcctg gcctctttac gggttatggc ccttgcgtgc cttgaattac | 2220 |
| ttccacctgg ctgcagtacg tgattcttga tcccgagctt cgggttggaa gtgggtggga | 2280 |
| gagttcgagg cctt | 2294 |

<210> SEQ ID NO 5
<211> LENGTH: 1782
<212> TYPE: DNA
<213> ORGANISM: Cytomegalovirus

<400> SEQUENCE: 5

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgagctcgg atccactagt ccagtgtggt ggaattctgc | 960 |
| agatcctgca gatggtgaca gggggaatgg caagcaagtg ggatcagaag ggtatggaca | 1020 |
| ttgcctatga ggaggcggcc ttaggttaca agagggtgg tgttcctatt ggcggatgtc | 1080 |
| ttatcaataa caaagacgga agtgttctcg gtcgtggtca caacatgaga tttcaaaagg | 1140 |
| gatccgccac actacatggt gagatctcca cttttggaaaa ctgtgggaga ttagagggca | 1200 |
| aagtgtacaa agataccact ttgtatacga cgctgtctcc atgcgacatg tgtacaggtg | 1260 |
| ccatcatcat gtatggtatt ccacgctgtg ttgtcggtga aacgttaat ttcaaaagta | 1320 |
| agggcgagaa atatttacaa actagaggtc acgaggttgt tgttgttgac gatgagaggt | 1380 |
| gtaaaaagat catgaaacaa tttatcgatg aaagacctca ggattggttt gaagatattg | 1440 |
| gtgagtaggc tagctctcta gtcgagtcca gcacagtggc ggccgctcga gtctagaggg | 1500 |
| cccgtttaaa cccgctgatc agcctcgact gtgccttcta gttgccagcc atctgttgtt | 1560 |
| tgcccctccc ccgtgccttc cttgaccctg gaaggtgcca ctcccactgt cctttcctaa | 1620 |
| taaaatgagg aaattgcatc gcattgtctg agtaggtgtc attcttattg aagcatttat | 1680 |
| cagggttatt gtctcatgag cggatacata tttgaatgta tttagaaaaa taaacaaata | 1740 |
| ggggttccgc gcacatttcc ccgaaaagtg ccacctgacg tc | 1782 |

GROWTH OF FOREIGN CELLS IN FETAL ANIMALS FACILITATED BY CONDITIONAL AND SELECTIVE DESTRUCTION OF NATIVE HOST CELLS

This application is a National Stage application of co-pending PCT application PCT/US2003/029251 filed Sep. 17, 2004, which was published in English under PCT Article 21(2) on Apr. 1, 2004, which claims the benefit of provisional application Ser. No. 60/411,790 filed Sep. 19, 2002. These applications are incorporated herein by reference in their entireties.

This invention was made with government funds from ATP grant no. 70NANB0H3008 from NIST, Department of Commerce. The U.S. government retains certain rights in the invention.

FIELD OF THE INVENTION

The invention relates to the growth and differentiation of foreign cells within a mammalian host. In particular, the invention relates to chimeric mammals that can be used to develop new drugs and vaccines, as well as to produce factors, drugs, and tissues for transplantation.

BACKGROUND OF THE INVENTION

Efforts to produce cells in vitro have met with limited success. While embryonic stem cells can be expanded indefinitely, it is difficult to expand differentiated cells. Moreover, it is currently not cost-effective to produce differentiated cells from stem cells in vitro.

The growth of foreign cells within an animal would provide substantial value in biotechnology. The production, expansion and isolation of cells using a non-human mammalian host would provide cells for infusion and transplantation, the production of drugs and factors for therapy, cells for tissue engineering and assays. The production of animals that are chimeric, and contain foreign cells would be useful for transplantation, models of disease, and for the functional assessment of a transgene.

Two factors make it challenging to grow foreign cells in animals, however. First, the foreign cells normally would be rejected by the host animal. Second, the foreign cells would need to compete with the native cells of the animal.

Cells have been grown in congenitally immune deficient animals. For example, human lymphocytes have been grown within SCID (severe combined immune deficiency) mice (1). These mice normally have a deficiency of B and T cells. However, the human lymphocytes are not appropriately functional and do not provide a normal immune response (2, 3).

Transgenic mice have been used to enhance engraftment with foreign cells. Rhim and Brinster produced transgenic mice with a defective urokinase plasminogen activator gene controlled by an albumin promoter. The native hepatocytes in these mice were defective and did not survive long. The defective hepatocytes were eventually replaced when foreign hepatocytes, including rat hepatocytes were injected (4). This model is not practical, however. Mice cannot be used as a source of donor organs. In addition, the pups had hypofibrinogenemia and usually died of neonatal hemorrhage (5).

SCID mice that are homozygous for urokinase plasminogen activator (uPA) have been engrafted with human hepatocytes (6). Due to the death of the mouse hepatocytes, the homozygous mice are difficult to keep alive. Heterozygous mice must be bred, and the homozygous offspring transplanted right after birth. The mice often die of liver failure before the human hepatocytes provide support. Because they lack a functional immune system, however this model has limited value for the development of vaccines.

Braun et al. used adult transgenic mice containing the suicide gene thymidine kinase to enhance engraftment with foreign cells (7). The thymidine kinase was under control of an albumin promoter and was expressed in the hepatocytes. The hepatocytes were normal until the prodrug gancyclovir was administered to adult mice. Most of the hepatocytes then died off, leading to regeneration with new hepatocytes. This system was an improvement over the uPA mouse model, because it permits controlled killing and turnover of the hepatocytes. But while engraftment was enhanced, overall survival was not generally improved. Following hepatic necrosis, most mice did not survive long enough to allow the differentiation and organization of the new hepatocytes. The small size of the mouse also limits the application of this system, because chimeric livers could not be produced for human transplantation.

Foreign cells have been infused into fetal animals, leading to limited engraftment. For example, limited engraftment of hematopoietic cells has been demonstrated in fetal sheep and monkeys (8) and by infusion into fetal mice, sheep, and pigs (9, 10, 11). Infusion of human hepatocytes or stem cells into fetal pigs has resulted in only limited engraftment (12). The intrauterine environment is favorable to engraftment with foreign cells, and the host naturally develops immune tolerance to the cells (13). The uterine environment is also naturally sterile. However, engraftment of foreign cells is very limited due to competition with the native host cells.

While transgenic mice can be readily produced to study diseases related to a specific gene, it is not practical to produce large animals. For example, pigs are several thousand times larger than mice and their generational time is about 10 times as long. To date, there has only been one herd of transgenic pigs produced for the study of human disease, retinitis pigmentosa (Petters et al., *Nature Biotechnology* 15, 965, 1997).

Thus, there is a need in the art for methods of engrafting foreign cells in fetal host animals.

DESCRIPTION OF RELATED PATENTS

U.S. Pat. No. 5,672,346 to Srour et al. teaches the infusion of hematopoietic stem cells into fetal non-human mammals leading to limited engraftment of hematopoietic cells. It does not provide a method for the elimination of native cells in the fetus.

U.S. Pat. No. 5,411,749 to Mayo et al. teaches the implantation of human lymphoid tissue into a mouse that is genetically immunodeficient for T and B lymphocytes. It does not provide for conditional elimination of native cells. The engrafted lymphocytes have limited function. For example, they are unable to provide a primary immune response to an antigen.

U.S. Pat. No. 5,698,767 to Wilson and Mosier teaches the implantation of human leukocytes into a SCID mouse, genetically immune deficient of T and B lymphocytes. The engrafted lymphocytes have limited function.

U.S. Pat. No. 6,211,429, "Complete oocyte activation using an oocyte-modifying agent and a reducing agent," to Z. Machaty and R. S. Prather, teaches the development of transgenic animals, including pigs, cows, sheep, mice, dogs, mice, and horses using nuclear transfer of cells transfected with a gene for growth hormone, placental lactogen, etc. It does not specifically teach the production of large transgenic animals with suicide gene or the induction of selective fetal tissue injury.

U.S. Pat. No. 6,147,276, "Quiescent cell populations for nuclear transfer in the production of non-human mammals and non-human mammalian embryos," to K. H. S. Campbell and I. Wilmut teaches the production of transgenic animals using nuclear transfer. It does not specifically teach the production of transgenic animals containing suicide genes or the selective and conditional injury to fetal tissues.

U.S. Pat. No. 6,291,740, "Transgenic Animals," to R. D. Bremel, A. W. S. Chan, and J. C. Burns, teaches the production of transgenic animals using perivitelline space injection of the transgene. It does not teach the use of a suicide gene for selective and conditional injury of fetal tissue.

SUMMARY OF THE INVENTION

One embodiment of the invention provides methods for enhanced growth of foreign cells within non-human mammals. The methods employ conditional and controlled reduction of select cells within a tissue of a fetal non-human mammal, followed by regeneration of the tissue with the foreign cells. The destruction of the fetal cells does not affect the corresponding cells in the maternal host or the foreign regenerating cells. The destruction of fetal cells is specific for the cells that are being replaced during tissue regeneration.

Another embodiment of the invention provides viable fetal non-human mammals with selective injury to target tissues, as well as maternal hosts comprising such fetuses. The fetuses are in a condition suitable for infusion with foreign cells, which can regenerate the injured target tissues. In some embodiments, fetal non-human mammals that contain a suicide transgene product produced in a target tissue have been exposed to the appropriate prodrug. In other embodiments, fetal non-human mammals contain suicide transgene products in all tissues and have been exposed to liposomes or immunoliposomes specific for the target tissue, which also can deliver the appropriate prodrug.

In another embodiment, the invention includes compositions and methods for enriching a population of cells from a chimeric animal for the foreign cells, by adding a prodrug that kills native cells expressing a suicide transgene.

The invention also provides fetal non-human mammals having a select cellular injury induced within the uterus of a normal maternal host. The cellular injury in the fetus is conditional and can be induced at the discretion of the user.

The invention provides methods for the growth of cells within fetal non-human mammals that have value for organ and cellular transplantation, production of factors by the foreign cells, and models of disease and physiology for development of new therapeutic agents.

The invention also provides mammals that express a suicide transgene product under the control of either a tissue-specific or a universal promoter, as well as methods for separating expanded foreign cells from native cells in a suspension.

In another embodiment of the invention, replacement cells are placed within a host animal during fetal development. The cells engraft and establish tolerance of the host animal to the replacement cells. The native host cells are subsequently depleted in a conditional and selective manner. This can be accomplished using transgenic animals expressing a suicide gene that would be injected with replacement cells in utero. Prodrug is be administered in a manner to conditionally and selectively destroy the native host cells. The prodrug can be administered on multiple occasions and administered after birth of the animals.

In yet another embodiment of the invention, select host cells are replaced with abnormal cells to produce models of human disease. The replacement cells can be from the same species as the host animal. In this case, the replacement cells can be transfected with the abnormal gene or they can have the test gene deleted ("knocked out"). The replacement cells can be from the same or from a different species, such as from a human with a congenital enzyme abnormality.

DETAILED DESCRIPTION

Overview

To achieve significant replacement of native cells in a host animal with foreign cells, it is preferable to selectively eliminate native cells of the host animal in a controlled fashion without harming the foreign engrafting cells. In addition, there should be physiologic support for the host animal during the period between elimination of native cells and engraftment with the foreign replacement cells. This invention achieves these goals by providing methods for selective and/or conditional destruction of cells in tissues of a fetal host without substantial destruction of cells in the maternal host mammal or injury of the foreign replacement cells (i.e., less than about 50, 45, 40, 35, 30, 25, 20, 15, 10, or 5% loss of maternal or foreign replacement cells). The maternal host mammal provides physiologic support while the foreign replacement cells engraft and regenerate the fetal tissue. The resulting chimeric or hybrid tissue is useful, for example, as a source of cells and tissue for transplantation, as well as for the production of factors and drugs for therapeutic purposes. The chimeric fetal host is useful, e.g. for the development of drugs and vaccines.

The invention also provides human cells for toxicology testing and research purposes. For example, human hepatocytes are in very short supply. Most available viable human cadavers are used liver transplants, and it is not possible to grow non-transformed human hepatocytes in culture. By growing and isolating human hepatocytes from hybrid pigs as disclosed herein, the invention can provide hepatocytes for research and for toxicology studies.

Methods of the invention provide multiple advantages for expanding and differentiating foreign replacement cells, including human cells, within a fetus of a non-human host mammal. A "fetus" is the unborn offspring of a viviparous animal. A fetus is distinguished from an embryo by the presence of the beginnings of all major structures (14). The fetal environment allows for growth of foreign replacement cells without immune rejection. The fetal environment also is ideal for the growth of new cells, providing growth factors needed for expansion of tissues and nutritional and physiological support for the temporary deficiency caused by the depletion of the target cells. The absence of the cellular deficiency in the maternal host is advantageous, allowing the fetuses to develop to term.

One or more tissues in the fetal host is injured and partially or completely eliminated, making the tissue receptive to regeneration with foreign replacement cells. Cells of most tissues can be regenerated using methods of the present invention. A "tissue" comprises a group of similarly specialized cells that perform a common function (e.g. liver, hematopoietic, endothelial, neural, epithelial, retinal, pigment epithelial, myocardial, skeletal muscle, smooth muscle, lung, intestine, kidney, endocrine, cartilage, or bone cells). A tissue can be either solid (e.g., liver) or dispersed (e.g., blood). Tissues that can be regenerated according to methods of the invention include, but are not limited to, liver, bone marrow, neural tissue, smooth muscle, skeletal muscle, cardiac muscle, skin, retinal pigment epithelium, pancreatic islets, endothelium, thymus, including thymic epithelium, lymphocytes, urogenital epithelium, renal tissues, stem cells and progenitor cells, pulmonary epithelium, bronchial epithelium, breast tissue, cartilage, bone, intestine, and intestinal epithelium.

Replacing native tissue cells with foreign tissue cells, such as hepatocytes, is useful for many purposes. The new hepatocytes can produce therapeutic proteins. A chimeric liver comprising human hepatocytes is useful as a source of cells for transplantation. The chimeric liver itself is valuable for transplantation and also provides a model system for development of therapies for diseases such as hepatitis. Human hepatocytes can be isolated from multiple pigs and infused into patients with chronic liver failure or congenital liver abnormalities.

A chimeric animal whose bone marrow cells are replaced with foreign bone marrow cells (e.g., human hematopoietic cells) can provide a cost effective bioreactor for producing human cells for transfusion, such as red blood cells, granulocytes, lymphocytes, dendritic cells, macrophages, megakaryocytes, platelets, etc. The chimeric animal also can be used as a model system for modulating the human immune response to antigens and for the development of new vaccines.

Foreign neural cells can be produced in host mammals for transplantation into patients with neurodegenerative diseases or spinal cord injuries.

Replacement of fetal host skin epithelium with foreign epithelium, including human epithelium, is a cost-effective method of producing skin for treatment of wounds, ulcers, and burns, for toxicology studies, and for the development of drugs and vaccines for pathogens that selectively infect human skin, such as the papilloma virus. Epithelial cells are also important in development of tolerance in the thymus. The development of human urogenital epithelium can be used in the reconstruction and transplantation of urinary bladders, urethras, and ureters.

Retinal pigment epithelium, such as human retinal pigment epithelium, produced in the fetal host mammal can be used to treat macular degeneration.

The replacement of pancreatic islets with foreign islets, including human islets, is valuable for transplantation into patients with diabetes.

Endothelial cells express many of the transplant antigens responsible for rejection. Thus, the replacement of fetal host mammal endothelial cells with foreign endothelial cells would be valuable for the transplantation of vascular organs such as hearts, lungs, kidneys, etc.

The replacement of host renal epithelial cells with foreign replacement cells such as human renal cells would produce better xenografts for transplantation, for production of human erythropoietin, and for control of blood pressure.

The growth of foreign stem cells and progenitor cells in place of the corresponding fetal host cells would be useful as a cost-effective bioreactor for the production of multipotential stem cells for stem cell therapy.

The replacement of pulmonary and bronchial epithelium with foreign replacement cells such as human pulmonary and bronchial epithelium would produce valuable organ transplants for the treatment of disorders such as chronic pulmonary failure and cystic fibrosis.

The replacement of breast epithelial cells with foreign replacement cells would be valuable for the production of therapeutic factors. The foreign replacement cells would be transfected for the desired protein. The protein could be easily harvested from the milk of a chimeric animal.

The growth of foreign cartilage and bone cells in host mammals would be useful for reconstructive surgery, as well as for the development of new drugs to treat disorders such as arthritis.

Human intestinal epithelial xenografts can be grown and used to treat congenital short gut syndrome and chronic intestinal diseases such as Crohn's Disease.

Transgenic Animals and Host Animals

Fetal and maternal host animals preferably are non-human mammals, such as non-human primates, artiodactyls, carnivores, rodents, or lagomorphs. Large mammals, such as pigs, sheep, cows, or non-human primates, are useful for producing organs or large numbers of cells suitable for human transplantation. Non-human primates are suitable from the standpoint of organ function and similarity to human cells. Amino acid sequencing of proteins typically demonstrate 90 to 98% homology with humans. While some of the lower primates, such as lemurs, have short gestation periods (132-134 days), the higher primates (chimpanzees, gorillas) have gestation periods approximating that of humans (267 days).

The artiodactyls (even-toed ungulates) include several domesticated animals such as pigs, sheep, goats, and cows. Many of their organs are similar to those of humans and have been shown to function within humans or non-human primates. The gestation periods vary between the members of this order. Pigs have a period of 114 days. Sheep have a period of 145 days. Cows have a gestation period of 282 days. Pigs, sheep, and cows offer specific advantages as a host animal. Pigs have large litters and short gestation periods. Fetal lambs are easy to inject with foreign replacement cells. Cows produce large offspring providing the potential for greater expansion. Also cells infused into one calf may circulate to the other calves through shared placental circulation. The pig is a preferred host.

The carnivores, including dogs, cats, etc., have several features that are potentially advantageous. Many have short gestation periods (cats about 65 days, dogs about 63 days), and their newborn are relatively well developed. Cats and dogs are often used as models of physiology and transplantation (22, 23).

Rodents, including rats, mice, etc., are useful for engraftment with foreign replacement cells because of their short gestation periods and rapid growth to maturity. For example, rats have a gestation period of only 21 days and grow to maturity in only 6 weeks. It is relatively easy to produce transgenic rodent animals, including knockout animals with deletion of a gene. Lagomorphs, which include rabbits and hares, share with rodents a very short gestation period and short maturation periods. Their larger size, however, make these animals better for producing larger organs and achieving greater expansion of the foreign replacement cells than the rodents.

Fetal hosts can be obtained by mating a transgenic male animal with a non-transgenic female animal. A "transgenic animal" comprises a "transgene," i.e., a gene that did not original in the transgenic animal (a foreign gene). A transgene may or may not be integrated into DNA of a host cell. The transgene preferably is integrated into the DNA of the transgenic animal's germ cells.

Transgenic animals can be made by any method known in the art, including nuclear transfer, intracellular sperm injection, and perivitelline space injection (33, 34). Either the male or female parent can carry the transgene and can be either heterozygous or homozygous. In one embodiment, a non-transgenic female mammal is bred with a transgenic male mammal containing a suicide transgene whose expression is controlled by a tissue-specific promoter. A transgenic male should be fertile and produce sperm with the suicide transgene in the genome. Preferably, the male is homozygous for the suicide transgene, so that all of the fetuses would then be heterozygous for the suicide gene. Heterozygous males can be used, though only one half of the fetuses would contain the suicide transgene.

If the prodrug is to be administered systemically to the maternal host, such as by injection into a sow, then a male transgenic animal should be bred with a wild-type, non-transgenic maternal host. Then, only the fetuses would express the suicide gene product. Optimally, a transgenic male would be homozygous, expressing the gene on both somatic chromosomes. Then all of the fetuses would carry the suicide gene in a heterozygous manner. The transgenic animal could be heterozygous as well, but only a portion of the fetuses would express the suicide gene.

For example, to grow human liver cells (hepatocytes) in pig livers, a non-transgenic female pig (gilt or sow) would be bred with a transgenic male pig (boar) a suicide gene controlled by a liver specific promoter such as an albumin or an α-fetoprotein promoter. The fetal pigs then express the suicide gene product in the target tissue, but the gilt or sow does not express it. Other tissue-specific promoters are known in the art and can be used as appropriate, such as the breast specific promoter for the whey acidic protein gene, tyrosinase related promoters (TRP-1 and TRP-2), DF3 enhancer, TRS (tissue specific regulatory sequences), tyrosine hydroxylase promoter, adipocyte P2 promoter, PEPCK promoter, CEA promoter, and casein promoter.

Destruction of Fetal Target Cells

Tissue and cellular depletion in the fetus leads to an advantageous environment for regeneration, by providing space in the tissue for new cell growth, production of growth factors favorable to cellular growth, protection from injury by the immune system, and protection from infection.

Ideally, the injury should be as early as possible without causing the death of the fetus. The fetal tissue should be subjected to injury and cellular depletion at a stage of gestation between the initial fetal development of the tissue and the birth of the host animal. The selective and conditional destruction of fetal target cells can be accomplished in various ways. For example, one could take advantage of the increased sensitivity of hematopoietic cells to radiation and administer localized radiation to the fetuses before infusing the replacement cells. Alternately, several proteins have been associated with early hematopoietic stem cells and progenitor cells, such as CD34 (23) and c-kit receptor (24). Transgenic mammals could be produced that express a suicide gene under the CD34 or c-kit receptor promoter. If a transgenic mammal is used with the suicide gene expressed universally, the prodrug can be delivered with liposomes containing stem cell factor (specific for the c-kit receptor) or an antibody to CD34.

Preferably the fetus is a chimeric animal with one transgenic and one normal parent. Typically, the male parent is a transgenic animal that expresses a suicide gene. A "suicide gene" is a gene that encodes an enzyme that converts a non-toxic prodrug into an active toxin that causes apoptosis. The suicide gene is typically viral or prokaryotic. Examples of suitable suicide genes include, but are not limited to, thymidine kinase (either wild-type or comprising a mutation), cytosine deaminase, carboxylesterase, carboxypeptidase, deoxycytidine kinase, nitroreductase, guanosine xanthin phosphoribosyltransferase, purine nucleoside phosphorylase, and thymidine phosphorylase. In the absence of the prodrug, expression of the suicide gene preferably has no toxic or other adverse effects on normal cellular metabolism (15).

Various prodrugs are available for selectively killing kill that express the corresponding suicide gene product. The products of the suicide genes act on a prodrug, converting them into a toxin. In the absence of the suicide gene product, the prodrug is relatively innocuous. Examples of prodrugs for thymidine kinase include gancyclovir, 6-methoxypurine arabinoside, and (E)-5-(2-bromovinyl)-2' deoxyuridine. An Example of a prodrug for cytosine deaminase is 5-fluorocytosine. An example of a prodrug for carboxylesterase is irinotecan. A prodrug for carboxypeptidase is 4-([2-chloroethyl][2-mesyloethyl]amino)benzyol-L-glutamic acid. Examples of prodrugs for deoxycytidine kinase include 4-ipomeanol cytosine arabinoside and fludarabine. Examples of prodrugs for guanosine-xanthin phosphoribosyl transferase include 6-thioxanthine and 6-thioguanine. An example of a prodrug for nitroreductase is 5-aziridin-2,4-dinitrobenzamidine. An example of a prodrug for purine nucleoside phosphorylase is 6-methylpurine deoxyribonucleoside. Examples of prodrugs for thymidine phosphorylase include 5'-deoxy-5-fluorouridine and 1-(tetrahydrofuryl)-5-fluorouracil.

The preferred embodiment for selectively and conditionally injuring fetal cells is to administer a prodrug to a fetal transgenic non-human mammal in a manner that injures cells of the target tissue without causing injury to the maternal host or to the foreign replacement cells regenerating the tissue. The transgenic mammal expresses a suicide transgene product in cells of the target. When exposed to the corresponding prodrug, these cells die.

The presence of the suicide gene product in the appropriate fetal tissue can be established by sampling tissues from fetal transgenic mammals and analyzing them with Western blots with specific antibodies.

If desired, subpopulations of target cells such as hematopoietic cells can be targeted. For example, B cells can be targeted in transgenic animals carrying a suicide transgene under the control of a CD19 promoter or by delivering the prodrug with immunoliposomes directed to the CD19 antigen. Nerve tissue can be removed surgically. Transgenic mammals Transgenic mammals using a promoter or immunoliposomes specific for fetal nerve tissue, such as calbindin-D28k, can be used (26).

Myoblasts differentiate into smooth muscle, skeletal muscle or cardiac muscle (cardiomyocytes). Selective destruction of the respective muscle can be accomplished by targeting specific promoters or antigens, such as sarcolemmal extracellular ATPase for smooth muscle (27), ryanodine receptor in skeletal muscle (28), and ventricular myosin light chain for cardiac muscle (29). Epithelial cells can be targeted based on the respective cytokeratins. Fetal retinal pigment epithelium can be removed surgically or targeted based on related proteins. Native pancreatic islets could be depleted with streptozotocin (18), or the beta cells could be targeted based on specific proteins, such as the insulin promoter. Endothelial cells can be targeted based on the promoter for von Willibrand's factor or antibodies to specific adhesion molecules such as ICAM-2 (30). Renal cells can be ablated with a suicide gene under a kidney specific promoter or antibodies to renal antigens. Native breast ductal cells can be targeted using breast specific promoters and antigens, such as 24-17.2 (31). Host intestinal epithelial cells in the base of the intestinal crypts are radiosensitive and express unique antigens (32).

The suicide gene product preferably is expressed in the appropriate tissue of the fetal host mammal at a level sufficient to be sensitive to a prodrug. The optimal dose of a prodrug depends on the prodrug, the particular suicide gene, the level of suicide gene expression in the target cells, zygosity of the fetal mammal, route of administration, and placental transport. Optimal doses can readily be determined by administering increasing doses of the prodrug to the pregnant mammal, assessing the effect on the target cells using standard pathology methods and assessing the effect on fetal survival using ultrasound and pathology techniques. The optimal dose would produce significant cell injury (>20%) with a minimum of fetal deaths (<15%). For example, when pregnant mice carrying fetal mice heterozygous for thymidine kinase under the albumin promoter (expressed in the liver) were injected with increasing doses of gancyclovir, it was found that an intravenous injection of 25 mg/kg produced significant hepatocyte necrosis but the fetal pups survived. At 50 mg/kg and higher, the fetal mice died.

The prodrug is administered to the fetal host at a gestation period when the target tissue is present and suicide gene is expressed in the fetal host, generally between the end of the first trimester and before birth of the animal. If the tissue-specificity is determined by the tissue-specific promoter, the timing may also be influenced by production of the transgene products. For example, the α-fetoprotein promoter is expressed in fetal hepatocytes. So the appropriate prodrug would deplete a portion of the fetal hepatocytes. AFP is also expressed in the yolk sac (19). Therefore, it would be preferable to delay administration of the prodrug until the yolk sac becomes insignificant, at the end of the first trimester.

Prodrugs that cross the placental barrier can be administered to the maternal host. Such drugs include gancyclovir (thymidine kinase), fludarabine(deoxycytidine kinase), and 1-(tetrahydrofuryl)-5-fluorouracil(thymidine phosphorylase). The placental transport of the proposed prodrug can readily be determined empirically. Following systemic administration to the maternal host, fetal tissues can be sampled for levels of the prodrug. With transgenic animals, the prodrug is administered systemically and the cellular injury in the fetal tissues can be assessed by standard histology. A dose response study establishes the optimal dose of prodrug, which produces significant tissue injury with maximum survival of the fetuses.

Prodrugs that do not cross the placental barrier can be administered directly to the fetal host. Methods for administering drugs to fetuses are known in the art. For pigs, for example, the optimal dose of gancyclovir is about 25 mg/kg (ranging from about 5 mg/kg to about 1000 mg/kg), and is administered at approximately 45 days gestation (from about 25 to 114 days).

The specificity of destroying the fetal target cells without injuring the foreign replacement cells or maternal host cells also can be accomplished in other ways. In another embodiment, transgenic fetal animals comprising a suicide transgene under the control of a universal promoter express the suicide gene product in all tissues. Suitable universal promoters include the MoMLV LTR, RSV LTR, Friend MuLv LTR, adenovirus promoter, neomycin phosphotransferase promoter/enhancer, late parvovirus promoter, Herpes TK promoter, SV40 promoter, metallothionen IIa gene enhancer/promoter, cytomegalovirus immediate early promoter, and cytomegalovirus immediate late promoter. Optionally, an inducible promoter can be used, e.g., a metallothionein gene promoter. Liposomes comprising a tissue-specific targeting ligand specific for the fetal target cell or immunoliposomes comprising a surface antibody that specifically binds to an antigen on a target cell are then injected into the fetal animal. The methods for production of liposomes and immunoliposomes containing prodrug are described in the literature (36, 17).

Specificity for the target tissue is determined by the ligand or antibody on the surface. The specific antibody or ligand would be determined by the system used. For example, to deplete fetal hepatocytes, liposomes would be produced carrying a ligand for the asialoglycoprotein receptor expressed on hepatocytes. The fetal tissues would be killed, but the other fetal tissues would not be affected because they do not have the receptor. The regenerating cells would not be affected because they would not contain the suicide gene product. The maternal hepatocytes would not be affected because of limited transport of the liposomes across the placenta.

The liposomes would not affect the foreign replacement cells that do not express the suicide gene product. The liposomes would not significantly affect the maternal host because either the maternal host does not express the suicide gene product or the liposomes do not cross the placental membrane into the maternal circulation.

The appropriate prodrug can be contained within the liposomes or immunoliposomes or can be administered separately. The optimal dose of a particular prodrug and the optimal dose of liposomes or immunoliposomes can be determined as described above.

For example, to replace pig hepatocytes with human hepatocytes, transgenic pigs can comprise a suicide gene, such as thymidine kinase, under the control of a universal promoter, such as a CMV promoter. The transgenic pigs (either female, male, or both) are bred. Liposomes are produced containing gancyclovir (optimal dose about 50 μM, range about 2 to about 500 μM). In another embodiment, transgenic pigs comprise a cytosine deaminase suicide gene under the control of the universal promoter. The liposomes or immunoliposomes contain 5-fluorocytosine (about 2 to about 500 μM). The liposomes or immunoliposomes can have a galactosylated surface that contains cholesten-5-yloxy-N-(4-((1-imino-2-B-d-thiolgalactos-ylethyl)amino)butyl)formamide (Ga1-C4-Cho1), which binds specifically to the asialoglycoprotein receptor expressed on the surface of hepatocytes (17). Alternatively an antibody that specifically binds to an asialoglycoprotein receptor can be linked to a liposome, for example using a polyethylene glycol link. The liposomes or immunoliposomes are injected into the fetal pig at about 45 days (range about 25 to about 114 days) or at the equivalent gestation period for other non-human mammals. Foreign replacement cells can be injected simultaneously or at a time shortly before or after the liposomes or immunoliposomes.

When a transgenic male is bred with a non-transgenic female, the suicide gene product is expressed only in the fetuses. It is not expressed in the maternal host or in the regenerating foreign replacement cells. Administration of a prodrug leads to destruction of the select fetal tissue cells.

In another embodiment, the transgenic mammals express the suicide gene product in most or all tissues. The specificity for the target cells is accomplished by placing the prodrug in the fetal mammal in a manner that it enters primarily the target cells.

In another embodiment, transgenic non-human mammals express the suicide gene product in most or all tissues. Specificity for the target cells can be accomplished by providing the prodrug directly to the tissue containing the target cells. For example, if the fetal hosts express thymidine kinase in all cells, including hepatocytes, the prodrug gancyclovir can be injected under ultrasound guidance into the liver, where the prodrug would kill the hepatocytes.

There are also methods for selectively and conditionally injuring and destroying fetal cells and tissue that do not use transgenic animals. In one implementation, the fetal cells would be transfected with gene therapy using a vector carrying the suicide gene. This could be a viral vector such as a defective adenovirus, or a non-viral vector such as liposomes or naked DNA.

The fetal tissues could be surgically removed. For example, much of the liver could be removed by surgical resection. This would lead to regeneration of the liver with the new cells.

Fetal cells also can be depleted by chemical means. For example, when streptozotocin has been injected into fetal rabbits and sheep, it destroys the pancreatic islets, leading to diabetes in the fetal animals (18). However, it has relatively little effect on the maternal islets.

Foreign Replacement Cells

"Foreign replacement cells" are defined as cells capable of proliferating and, optionally, differentiating into mature cells within a tissue to regenerate the tissue. Such cells include differentiated cells, progenitor cells, tissue-specific stem cells, multipotent stem cells, and omnipotent stem cells. The cells may be from the same species or from a different species (xenogeneic) and may be primary cells or cells of a cell line. Cells from the same species can be used to produce factors in the chimeric animal that have therapeutic value. For example, pig hepatocytes can be transfected with human factor VIII. When these cells replace the native pig hepatocytes, the chimeric animal would produce human factor VIII. Chimeric animals comprising cells from a different species can be used as models for human physiology and disease, for the development of new drugs and vaccines, for the production of human factors for therapeutic use, and to provide cells and organs for transplantation. Foreign replacement cells may or may not be genetically modified.

Tissue based stem cells have the ability to proliferate and differentiate into the corresponding tissue cells. For example, pancreatic duct cells can differentiate into islets of Langerhans. Hepatic oval cells can differentiate into hepatocytes.

Adult stem cells and certain tissue-based stem cells are known to have plasticity, being capable of differentiating into other types of cells. For example, hematopoietic stem cells can differentiate into endothelial cells, neurons, glia, hepatocytes, cardiomyocytes, renal tubular cells, pulmonary epithelium, intestinal cells, skin epithelium, bone, cartilage, muscle, fat, and brain (20, 21).

Embryonic stem cells have the ability to proliferate indefinitely and differentiate into any tissue. Either the embryonic stem cells, cell lines produced from embryonic stem cells, or progenitor cells derived from the embryonic stem cells or cell lines would regenerate the injured fetal tissue.

Typically, foreign replacement cells are injected into the fetus in a sterile manner using technology known to those active in the field. The cells should be of sufficient number to regenerate the tissue. Generally more cells are more effective than fewer cells. The cells capable of regenerating the tissue should be present at a time following the injury and destruction of target host cells. They may be injected before the injury, provided that they survive until after the injury occurs. Optimally, the cells should be placed in the fetal host before the birth of the host mammal, in order to benefit from the protection provided to the fetus by the maternal host and immune hyporeactivity to the foreign replacement cells.

For example, human cells capable of regenerating the liver, such as hepatocytes, liver progenitor cells, or hematopoietic stem cells, can be injected into fetal pigs. The optimal number of cells injected depends on the source and can be determined empirically using routine screening methods. For pigs, optimally the cells are injected at 52 days gestation or seven days after the prodrug (range 25 to 114 days gestation). The optimal dose of human hepatocytes is $5 \times 10^6$/pig (range $1 \times 10^5$ to $5 \times 10^7$ cells/pig). The optimal number of liver stem cells is $5 \times 10^5$/pig (range 1 to $5 \times 10^7$/pig) (16). Bone marrow and cord blood provides a source of pluripotential progenitor cells that can differentiate into hepatocytes. The optimal dose of cord blood is $2.5 \times 10^7$ nucleated cells/pig (range $1 \times 10^6$ to $10^8$). The cells preferably are injected using a sterile technique. Ultrasound guidance can be used. The injection technology is generally known to those familiar with the art.

Methods for Separating and Enriching a Foreign Replacement Cell Population from a Mixture of Foreign Replacement Cells and Host Mammal Cells The invention provides methods for efficiently removing host cells from a cell suspension containing both host cells and foreign replacement cells. For example, if human hepatocytes were grown within a fetal transgenic non-human mammal containing a suicide gene product, it would be advantageous to separate the non-human mammal cells from the human cells. The human cells could then be used, for example, for transplantation into patients. Human cells also can be used in devices; for example, human hepatocytes can be used artificial livers, providing temporary life support for patients in liver failure.

In one embodiment, a mixture of cells from a tissue of a transgenic non-human mammal containing a suicide gene product and non-transgenic foreign replacement cells is placed in a liquid medium containing a prodrug for that activates the suicide gene. In the presence of the suicide transgene product, the transgenic cells die while the foreign replacement cells remain viable. For example, if the suicide transgene is thymidine kinase, gancyclovir or a gancyclovir analogue is added to the culture medium (optimally at about 20 µM, ranging from about 1 µM to about 10 µM). After a period of time (e.g., from about 1 to about 20 days, preferably about 7 days), the non-human mammalian cells would die out, leaving a suspension enriched for foreign replacement cells. Dead non-human mammalian cells and cell fragments can be separated from live foreign replacement cells using established technology well known to those skilled in the field.

In another embodiment, non-human mammalian host cells contain a transgene that facilitates separation of these cells from the foreign replacement cells. For example, the transgene can encode green fluorescent protein (GFP). The non-human mammalian cells can then be separated from the foreign replacement cells that do not express GFP by fluorescence activated cell sorting.

In another embodiment, a mixture of cells from a transgenic mammal containing a suicide gene product and non-transgenic foreign replacement cells is cultured in medium containing a prodrug for the suicide gene product. The transgenic cells die, while the foreign replacement cells remain viable. For example, gancyclovir or an analogue can be added to a culture of a mixture of human hepatocytes transgenic pig cells comprising thymidine kinase (optimally 100 mg/l or 4 mM gancyclovir, range 2 to 1000 mg/l). After a period of time (optimally 7 days, range 1 to 20 days), the pig cells die, leaving a suspension enriched for human hepatocytes.

To purify foreign replacement cells from native host cells, the suicide gene product could either be expressed in select cells under a specific promoter or expressed globally under a universal promoter. However, global expression would permit more thorough purification. In the above example, pig cells with the suicide gene under an albumin promoter would permit elimination of the native hepatocytes, the primary contaminating cell. A suicide gene controlled by a universal promoter, however, would help eliminate other cells as well, including endothelial cells, Kupfer cells, etc.

There are multiple methods for separating dead cells from viable cells. If viable cells adhere to the culture flask, dead cells can be removed by removing the media and washing the adherent cells with media. Dead cells also can be removed by centrifuging the mixture over a density gradient.

Other transgenes can also facilitate depletion of the native cells from the foreign replacement cells, such as new antigens allowing for antibody mediated separation, ligands for receptors, and proteins that chelate iron, allowing for magnetic removal.

A mixture of cells procured from the chimeric host mammal to determine the presence and amount of host mammalian cells remaining after purification procedures. Cells from the transgenic mammal contain a unique transgene in the genome, allowing for sensitive polymerase chain reaction assays using primers specific for the transgene. Routine and quantitative PCR assays are well known to those in the field. Expression of transgene products permits easy quantitation of the remaining cells. For example, the expression of green fluorescent protein in the host mammalian cells permits quantitation of the host cells by flow cytometry.

Normal Maternal Host Comprising a Fetus Having a Targeted Cellular Injury

The invention provides a normal maternal host comprising a fetal non-human mammal in which one or more targeted cellular injuries has been induced. The cellular injury in the fetus is conditional and can be induced at the discretion of the user. This provides an efficient and cost effective bioreactor for growing foreign replacement cells, including transfected cells for production of therapeutic factors, models for the study of disease and development of drugs and vaccines, and a source of cells and organs for transplantation.

The combination of normal maternal host and fetal non-human mammal comprising such a cellular injury provides advantages for growing foreign replacement cells within the fetal host, including a structural framework for regeneration with foreign replacement cells with space for the foreign replacement cells, appropriate growth factors, physiologic support from the maternal host, protection from immune rejection, and a sterile environment. The host species should be fertile and able to reproduce. Injury to target tissue in the fetal non-human mammal can be controlled by the user and can be specific for select cells in the fetus but not in the maternal host or regenerating cells. Such a fetus can continue to live for an extended period within the uterus of the maternal host mammal. The fetus preferably is receptive to the placement of regenerating cells during fetal development.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Growth of Human Hepatocytes in Fetal Pigs

These studies demonstrate that human hepatocytes survive in fetal pigs and produce human liver proteins.

Pig livers can provide temporary support for patients with acute liver failure. Because many proteins produced by the liver are species specific, however, these xenografts might not be adequate for long-term support. To produce chimeric pig livers repopulated in part with human hepatocytes, fetal pigs were infused with human hepatocytes.

Human hepatocytes were injected into the livers of pre-immune fetal pigs (45 days gestation) using ultrasound guidance. Frozen and thawed human hepatocytes were infused into 8 piglets (2 or $5 \times 10^6$ cells) from two litters. The two piglets of another litter were infused with human hepatocytes transformed with SV40 ($10 \times 10^6$ cells). After farrowing, a fourth litter was euthanized at 5 days and the tissues analyzed. Piglets of the first three litters were followed by testing their sera for human liver proteins. Alpha-1 antitrypsin ($\alpha$1-antitrypsin) was detected with Western Blots. Serum amyloid A (SAA) was quantified by ELISA. Tissues were evaluated using PCR to detect class I human leukocyte antigen in the major histocompatibility complex and immunoperoxidase staining using a monoclonal antibody to detect human albumin.

Two injected piglets from the first litter were stillborn. Their tissues, however, contained human DNA. The other three injected pigs were healthy, as were the five chimeric pigs from the other two litters. All showed evidence of human hepatocytes, with levels of human SAA at 0.1% to 0.9% of normal human levels. Alpha-1 antitrypsin was assessed in the serum of three pigs, which had levels of $\alpha$1-antitrypsin between 1 and 22% of normal human levels.

The spleens of all five pigs from the first litter contained human DNA. Immunoperoxidase staining of tissues of the euthanized pigs for human albumin showed individual human hepatocytes in the spleen and scattered lobules in the liver. The lobules had a normal sinusoidal architecture. SAA was detected in the sera of the other five pigs for up to 90 days (as long as these pigs were followed).

These studies demonstrate that human hepatocytes survive in fetal pigs and produce human liver proteins. Based on the cells observed in the liver and spleen, it is estimated that the human hepatocytes expanded 29- to 90-fold. Apparently, the native pig hepatocytes limited the engraftment of the human cells, because engraftment of human cells amounted to less than 3% of the pig liver.

EXAMPLE 2

Growth of Human Hepatocytes from Marrow or Cord Blood Cells in Fetal Pigs

This example demonstrates that both human bone marrow and cord blood are appropriate sources for hepatocytes.

Hematopoetic stem cells demonstrate plasticity, with the ability to differentiate into somatic cells. In this study, human marrow or cord blood cells were infused into fetal pigs. The resulting chimeric pigs were assessed for evidence of human hepatocytes and serum proteins secreted by the human hepatocytes.

Human marrow cells (1.5 to $3 \times 10^7$/pig) or cord blood cells (1-1.5$\times 10^7$/pig) were injected into the livers of pre-immune fetal pigs (45 days gestation) using ultrasound guidance. The marrow was depleted of 75% of the CD4$^+$ and CD8$^+$ T cells. The pigs were delivered by Cesarean section at term. At 1 to 2 weeks of age, serum was evaluated for human serum amyloid A (hSAA) and human albumin (hAlb) using an ELISA. Paraffin-embedded sections of liver were stained by immunoperoxidase for human albumin using an immunoperoxidase method.

Serum was available from 17 pigs injected with human marrow and 13 pigs injected with cord blood cells. Fourteen of the marrow-injected pigs were considered chimeric. The concentration of hSAA was 62±152 ng/ml for the marrow-injected pigs. The human albumin in the marrow-injected pigs was present at an average concentration of 7±8 µg/ml. Immunohistochemistry of liver sections demonstrated lobules of hepatocytes expressing human albumin, with apparent cellular expansion. The hepatocytes showed normal sinusoidal architecture. The periportal regions, however, did not contain hepatocytes expressing human albumin. The area of tissue stained was less than 3% of the total. The pigs injected with human cord blood cells showed similar results.

EXAMPLE 3

Expression of a Suicide Gene Product in a Cell Line and Sensitivity to a Prodrug This example shows that selective expression of a suicide gene product and selective killing of target cells can be controlled by a tissue-specific promoter.

Liver cell lines were transfected with suicide genes controlled by either an albumin or an α-fetoprotein promoter. Albumin and α-fetoprotein are expressed primarily in hepatocytes, with α-fetoprotein expressed more in immature hepatocytes and liver carcinoma lines.

Mouse and human liver cell lines were transfected with constructs containing delta thymidine kinase under the control of either a porcine albumin or α-fetoprotein (AFP) promoter. The mouse cell line (TIB73) is a line of mature hepatocytes in which albumin is expressed. The human cell line (Huh-7) is a line of hepatocellular carcinoma cells that express predominantly AFP. The transfected cells were tested for thymidine kinase by Western blot.

To assess the function of mutated thymidine kinase, Huh-7 cells were stably transfected with AlbxTK. Transfected cells were selected using 200 µg/ml Zeocin. Transfected cells as well as untransfected cells were plated in duplicate in 24-well plates at a 40 percent confluence ratio. Gancyclovir was added to the cells in the culture media at different concentrations (4 µM, 8 µM, and 16 µM. After 5 days, the cells were trypsinized, washed twice in PBS, and stained with propidium iodine for FACS analysis.

Figure 1:
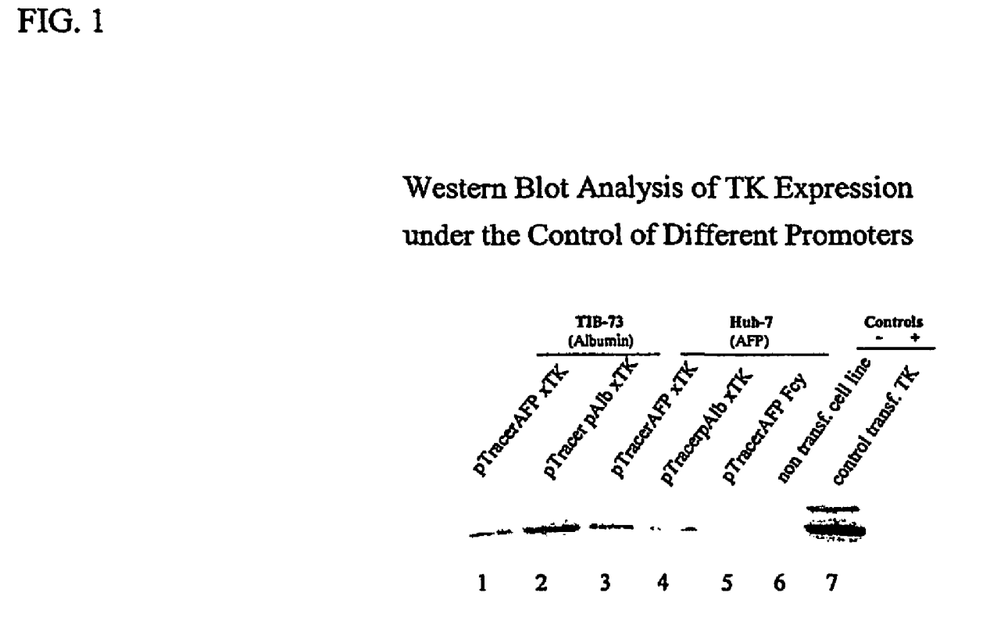
FIG. 1. Western blot analysis of TK expression under the control of different promoters.

As shown in FIG. 1, thymidine kinase was expressed by both the mouse hepatocyte line (TIB73) and the human hepatocellular carcinoma line (Huh-7). Expression with the albumin promoter was greater with the mature hepatocyte line, while the expression with the α-fetoprotein promoter was greater in the hepatocellular carcinoma line. While PCR analysis demonstrated the presence of the transgene in non-liver lines (fibroblasts, renal tubular epithelial line PK-15) transfected with these plasmids, expression of thymidine kinase was not observed by Western blot.

Incubation with 8 or 16 µM gancyclovir caused significantly more cell death at 5 days. The Huh-7 cells were entirely killed at 7 days. Gancyclovir had only a minimal effect on non-transfected cells.

EXAMPLE 4

Selective Destruction of Fetal Hepatocytes in Using a Suicide Gene Under Control of a Tissue-specific Promoter This example demonstrates that selective tissue injury of the target cells can be produced in a fetal host using a suicide transgene under the control of a target tissue-specific promoter without significantly affecting the maternal host. It also demonstrates production of fertile males that carry the transgene and that the prodrug gancyclovir crosses the placental barrier to cause injury in the fetal target tissues.

Transgenic mice were produced with the FVB strain containing the mutated thymidine kinase transgene under the albumin promoter. The males from the F2 generation were fertile and homozygous. These males were bred with non-transgenic FVB mice. At 14 days gestation, gancyclovir (0 to 100 mg/kg body weight) was injected intravenously into the pregnant mice. Tissues from the mothers and fetuses were analyzed by histology.

No injury was observed in the fetuses or mothers injected with vehicle. At 25 mg/kg, the fetal mice had partial necrosis of the hepatocytes. At 50 and 100 mg/kg, there was massive hepatic necrosis. There was no observable injury to the hepatocytes of the mother or to the non-liver tissues in the fetal mice at any dose.

EXAMPLE 5

Immunoliposome Delivery of Prodrug to Cell Lines Containing a Suicide Gene Product and an Appropriate Surface Antigen One implementation of the invention uses transgenic host mammals that express the suicide gene product in all tissues. Tissue-specificity is provided by immunoliposomes carrying an antibody or liposomes with a ligand specific for a select receptor. This example demonstrates the relative specificity provided by immunoliposomes.

Immunoliposomes were produced with mouse anti-pig Class I SLA antigen on the surface and containing gancyclovir at concentrations from 0 to 100 µM. The immunoliposomes were incubated with cell cultures of PK-15 (pig renal tubular cell line) transfected with thymidine kinase under the control of a universal promoter or with Huh-7 (human hepatocyte line) with thymidine kinase under the control of an α-fetoprotein promoter.

The immunoliposomes killed cells from the pig cell line, which expresses class I SLA antigen, in a dose response manner. The immunoliposomes did not significantly affect the human cell line, which contained the suicide gene product but not the class I SLA antigen. Immunoliposomes without gancyclovir did not affect either cell line.

EXAMPLE 6

Development of Transgenic Pigs Containing a Suicide Gene

This example demonstrates the construction of herds of transgenic pigs containing suicide genes.

Briefly, fibroblasts from 35-day-old fetal pigs were cultured and then transfected with a suicide transgene (either a mutated thymidine kinase or cytosine deaminase) using electroporation. Colchicine was added to arrest the transfected fibroblasts in G2/M phase. Swine oocytes were cultured, and the polar bodies were removed. Transfected fibroblasts were inserted into oocytes using a micromanipulator. Following activation, embryos were implanted into surrogate sows at estrus. The litters were monitored by ultrasound. At term, the pigs were delivered by Caesarean section.

Cord blood from the transgenic pigs were analyzed for the presence of the transgene using PCR. The transgenic pigs were bred, and the F1 and F2 fetal pigs were analyzed by Western blot for the presence of the suicide gene. Sensitivities to the corresponding prodrug (gancyclovir for thymidine kinase, 5-fluorocytosine for cytosine deaminase) were assessed in other sows carrying the suicide gene.

Figure 2:
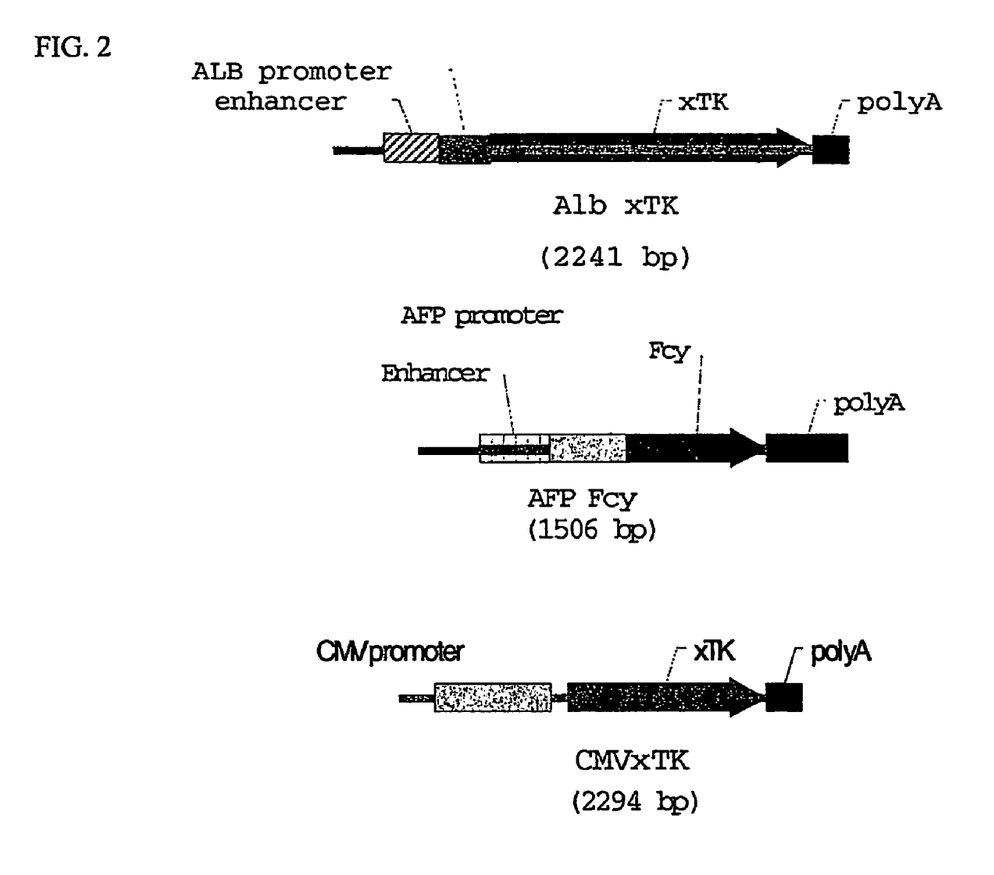
FIG. 2. Genetic constructs for suicide transgenes.

The genetic constructs were used for the suicide transgenes are shown in FIG. 2. The nucleotide sequence of a porcine albumin promoter is shown SEQ ID NO:1. xTK is a mutated version of a Herpes simplex virus (HSV) thymidine kinase gene that was mutated by two rounds of site-directed mutagenesis, resulting in the replacement of adenosine for cytosine at nucleotides 130 and 180, to prevent male sterility. The nucleotide replacements resulted in a codon change such that a leucine replaces a methionine. These changes do not affect the enzymatic activity of the gene, because the catalytic pocket is located far away from the mutations. The four constructs also contain green fluorescent promoter under a universal promoter. This aids in the analysis of chimeric animals and in the separation of native pig cells from foreign replacement cells.

Three transgenic male pigs with the Alb-xTK transgene were delivered. Western blot analysis of fetal F1 pigs demonstrated the presence of thymidine kinase in the liver. Transgenic pigs were delivered and raised with the AFP-cytosine deaminase transgene, CMV-xTK transgene, or CMV-cytosine deaminase transgene. Western blot analysis confirmed expression of the product of the AFP promoter-controlled transgene in the fetal liver and of CMV promoter-controlled transgene in multiple tissues (liver, lung, heart, brain).

The four herds of transgenic pigs are the first transgenic pigs containing suicide genes. This is the first use of porcine tissue-specific promoters (albumin and α-fetoprotein), and the first pigs containing the mutated thymidine gene.

EXAMPLE 7

Enhanced Engraftment of Human Hepatocytes in Fetal Pigs with Suicide Transgenes After Exposure to a Prodrug The fetal environment is most suitable for growing foreign replacement cells. Growth factors are abundant, the environment is sterile, and rejection of the foreign replacement cells does not occur. The maternal host provides physiologic support. However, the native cells severely limit the amount of engraftment. To overcome this problem, native fetal pig liver cells are killed by administering the prodrug gancyclovir to the sow. Because the sow does not contain the transgene, the sow liver cells are not affected. The prodrug crosses the placental membrane and kills a portion of the pig liver cells in those fetal pigs containing the transgene. This is followed by infusion of human cord blood cells, which provides a source of progenitor cells to regenerate the fetal pig liver with human hepatocytes.

A non-transgenic sow is bred with a boar that is hemizygous for a mutated thymidine kinase transgene under the control of an albumin promoter. Pregnancy is confirmed with ultrasound and gancyclovir (100 mg/kg, i.v.) is administered at 40 days gestation. A laparotomy is performed at 45 days. Each pig is infused with $10\times10^6$ human cord blood cells. The piglets are delivered at term by Caesarean section. Blood is drawn from each fetal pig and analyzed for the presence of the suicide transgene using PCR. Serum is tested for the presence of human liver proteins, including albumin, α1-antitrypsin, and serum amyloid A. Sections of liver are frozen and stained for human albumin.

Piglets without the thymidine kinase transgene express levels of human albumin, α1-antitrypsin inhibitor and serum amyloid A at less than 1% of levels seen in humans. Piglets with the thymidine kinase suicide transgene have levels of the three proteins at 20 to 37% of normal human values. Sections of liver from pigs without the suicide transgene show scattered lobules of human hepatocytes (e.g., less than 2% of the total liver). Liver sections from pigs with the thymidine kinase suicide gene show large areas engrafted with human hepatocytes (e.g., an average of 25% of the total liver).

Thus, extensive engraftment of the fetal pig liver with human hepatocytes can be achieved by exposing fetal pigs having a thymidine kinase suicide transgene to the prodrug gancyclovir, whereas pigs without the suicide transgene show very limited engraftment.

EXAMPLE 8

Conditional and Selective Destruction of Host Cells after an Animal is Born

Transgenic boars are produced that express the suicide gene thymidine kinase under the albumin promoter. Accordingly, the suicide gene is preferentially expressed in hepatocytes, particularly in juvenile and adult pigs.

The transgenic boars (preferably homozygous for the suicide gene) are bred with wild type gilts or sows. During fetal development (30 to 90 days gestation, preferably 40 to 60 days), the fetal pigs are injected with progenitor or stem cells that develop into human hepatocytes. They may be human hepatocytes from isolated human cadavers. One to 20 million hepatocytes (preferably 2 to 5 million) are injected into the liver or abdomen of each fetal pig.

After birth of the pig, the serum or liver may be examined for evidence of human cells. The prodrug for thymidine kinase, such as gancyclovir is administered to the pig, at a dose known to destroy a portion of the of pig hepatocytes. Following recovery, the prodrug may be administered on multiple occasions.

EXAMPLE 9

Conditional and Selective Destruction of Host Cells after an Animal is Born

Transgenic mice are produced that express the thymidine kinase gene under the albumin promoter. The male mice are bred with wild type females. Human hepatocytes ($2\times10^6$ per fetal mouse) are injected at 17 days gestation, just prior to delivery. At 14 days of age, the mice are injected with gancyclovir (50 mg/kg) on days 1 and 3 or with the vehicle. Thirty days later, the mice are sacrificed. The mice treated with gancyclovir show substantially greater engraftment with human hepatocytes than the controls not treated with gancyclovir.

EXAMPLE 10

Replacement of Host Cells with Transfected Cells to Produce Models of Human Disease Conditional SCID Pig with Transgenic Pigs Expressing Thymidine Kinase under the jak3 kinase Promoter.

Mice and humans with X-linked immune deficiency have nearly absent T lymphocytes and deficient B lymphocytes. In both species, the X-SCID is associated with a mutation of the jak3 tyrosine kinase. Sequencing of the promoter shows a high degree of conservation between humans and mice (32). In contrast to typical SCID models, the conditional SCID pigs are immune competent until treated with the prodrug. They are therefore much easier to produce. The conditional SCID pig is very useful for many different purposes, including development of stem cell transplants, development of surrogate tolerogenesis, or cancer research. For example, the conditional SCID pigs can be made immune deficient and transplanted with a human tumor line that metastasizes to the liver. New procedures for ablation of metastatic tumors can then be tested.

The porcine promoter for jak3 is isolated from a cDNA library and expanded using primers flanking the 5' and 3' regions. The porcine sequence is determined. The albumin promoter in the pTracerpAlbxTK plasmid is replaced with the porcine jak3 promoter. Transgenic pigs are produced and screened for the transgene in the bone marrow. Bone marrow is further screened for mRNA by RT-PCR.

The transgenic herd is expanded through cloning or breeding.

Transgenic pigs are treated weekly with Gancyclovir. The peripheral blood is evaluated at weekly intervals for T cells, B cells and immunoglobulins.

EXAMPLE 11

Replacement of Host Cells with Transfected Cells to Produce Models of Human Disease Conditional Knockout and Replacement of Endothelial Cells with Transgenic Pigs Expressing Thymidine Kinase under the von Willebrand Promoter.

The primary target of rejection in organ xenografts is the endothelium. Most work with transgenic pigs has focused on modifying the endothelium, i.e., complement inhibitors and knockout of the alphaGa1 antigen. The pace of this research, however, is limited by the time required to produce a new line of transgenic pigs. In vitro tests can be performed with transfected cultured endothelium. There are no good in vitro assays of acute vascular rejection, however. A transgenic pig herd with a suicide gene expressed in the endothelium can be produced, which allows replacement of native endothelium with a test endothelium that is genetically modified. With this system, the hybrid pig organ can be tested by transplantation. Multiple modifications can be compared. When the optimal genetic modification is achieved, transgenic pigs for clinical use can be produced. The pace of xenotransplant research can be accelerated by a factor of 10. These pigs are also valuable for studying hematopoiesis, atherosclerosis, and to develop better stents.

The porcine von Willebrand promoter is isolated and inserted into the pTracerpAlbxTK plasmid in place of the porcine albumin promoter. Fetal pig fibroblasts are transfected. Transgenic pigs are produced by nuclear transfer. At delivery, cord blood is screened by PCR for the transgene in the DNA. The umbilical cord is infused with trypsin and the endothelial cells cultured. The cells are analyzed by RT-PCR and Western blot for the production of the TK mRNA and enzyme. The herd is expanded through cloning or breeding.

Endothelial progenitor cells are isolated from cord blood of non-transgenic pigs using Meltenyi beads and antibodies to porcine CD34 or CD31. The progenitor cells are transfected with yellow gfp under a universal CMV promoter. The transfected cells are infused into fetal pigs. The pigs are subsequently administered the prodrug Gancyclovir to deplete a population of native endothelial cells. Pigs are euthanized. Lung and liver sections are cannulated, washed and perfused with trypsin to isolate endothelial cells. The relative number of cells with yellow fluorescence is quantified by flow cytometry and compared with similar engraftment studies performed with nontransgenic pigs.

EXAMPLE 12

Replacement of Host Cells with Transfected Cells to Produce Models of Human Disease Replacement of Native Animal Cells with Cells from a Human with Congenital Abnormality.

To produce an animal model of Gaucher's disease, hepatocytes from a human cadaver are isolated and injected into fetal transgenic pigs expressing a suicide gene, such as thymidine kinase under the albumin promoter. Later, the native pig hepatocytes are depleted by administered a sublethal dose of the prodrug gancyclovir. This can be done on multiple occasions.

EXAMPLE 13

Replacement of Host Cells with Transfected Cells to Produce Models of Human Disease Replacement with Cells in which the Test Gene Has Been Inserted between Cre-Lox or FLP Codes by the Appropriate Recombinase Enzyme.

To produce more predictable outcomes, the replacement cells can come from a herd of transgenic animals with the Cre-Lox or FLP marker genes. The appropriate recombinase enzyme can replace the DNA between the markers with the desired transgene. Herds can then be readily produced that compare different genes for the development of the disease. For example, different apolipoproteins can be produced by different herds and the development of coronary atherosclerosis determined.

All patents, patent applications, and scientific references cited in this disclosure are expressly incorporated by reference in their entireties.

REFERENCES

1. McCune, J., Kaneshima, H., Krowka, J., Namikawa, R., Outzen, H., Peault, B., Rabin, L., Shih, C. C., Yee, E., Lieberman, M., and et al. The SCID-hu mouse: a small animal model for HIV infection and pathogenesis. [Review]. Annu Rev Immunol 9, 399-429. 1991.
2. Aaberge, I. S., Michaelsen, T. E., Rolstad, A. K., Groeng, E. C., Solberg, P., and Lovik, M. SCID-Hu mice immunized with a pneumococcal vaccine produce specific human antibodies and show increased resistance to infection. Infect. Immun. 60(10), 4146-4153. 1992.
3. Cao, T. and Leroux-Roels, G. Antigen-specific T cell responses in human peripheral blood leucocyte (hu-PBL)-mouse chimera conditioned with radiation and an antibody directed against the mouse IL-2 receptor beta-chain. Clin. Exp. Immunol. 122(1), 117-123. 2000.
4. Rhim J A, Sandgren E P, Palmiter R D, Brinster R L. Complete reconstitution of mouse liver with xenogeneic hepatocytes. Proc. Natl. Acad. Sci. 92:4942-6, 1995.
5. Sandgren E P, Palmiter R D, Heckel J L, Daugherty C C, Brinster R L, Degen J L. Complete hepatic regeneration after somatic deletion of an albumin-plasminogen activator transgene. Cell 66:245-56, 1991.
6. Mercer, D. F., Schiller, D. E., Elliott, J. F., Douglas, D. N., Hao, C., Rinfret, A., Addison, W. R., Fischer, K. P., Churchill, T. A., Lakey, J. R., Tyrrell, D. L., and Kneteman, N. M. Hepatitis C virus replication in mice with chimeric human livers. Nat. Med. 7(8), 927-933. 2001.
7. Braun, K. M., Degen, J. L., and Sandgren, E. P. Hepatocyte transplantation in a model of toxin-induced liver disease: variable therapeutic effect during replacement of damaged parenchyma by donor cells. Nat. Med. 6(3), 320-326. 2000.
8. Zanjani, E. D., Ascensao, J. L., Flake, A. W., Harrison, M. R., and Tavassoli, M. The fetus as an optimal donor and recipient of hemopoietic stem cells. Bone Marrow Transplant 10 Suppl 1, 107-114. 1992.
9. Pixley, J. S., Zanjani, E. D., Shaft, D. M., Porada, C., and MacKintosh, F. R. Prolonged Hematopoietic Chimerism in Normal Mice Transplanted in utero with Human Hematopoietic Stem Cells. Pathobiology 66, 230-239. 1998.
10. Srour, E. F., Zanjani, E. D., Brandt, J. E., Leemhuis, T., Briddell, R. A., Heerema, N. A., and Hoffman, R. Sustained human hematopoiesis in sheep transplanted in utero during early gestation with fractionated adult human bone marrow cells. Blood 79, 1404-1412. 1992.
11. Beschorner, W. E., Qian, Z., Mattei, P., Hess, A. D., Colombani, P. M., Sciscione, A. C., Khouzami, A., Blakemore, K. J., and Burdick, J. F. Induction of human chimerism and functional suppressor cells in fetal pigs: feasibility of surrogate tolerogenesis for xenotransplantation. Transplant. Proc. 28:648-9, 1996.
12. Beschorner, W. E., Thompson, S. C., Yang, T., Cederberg, C., Fox, I. J., Strom, S. C. Human hepatocytes from fetal pigs infused with hepatocytes or marrow. Cell Transplant Society, 10$^{th}$ Anniversary Congress, 2001, p. 83.
13. Billingham R, Brent L, and Medawar P. Quantitative studies on tissue transplantation immunity III. Actively acquired tolerance. 1956; Proc R Soc Lond [Biol]. 238: 357-415.
14. Moore K. L. The Developing Human. Clinically Oriented Embryology. W. B. Saunders Company. 1973, pp.1.
15. Morris J. C., Touraine R, Wildner O., and Blaese, R. M. Suicide Genes: Gene Therapy Applications Using Enzyme/Prodrug Strategies. In Friedmann T., Ed. The Development of Human Gene Therapy. Cold Spring Harbor Laboratory Press, Cold Spring Harbor, N.Y., 1999, pp. 477.
16. Matsusaka, S., Toyosaka, A., Nakasho, K., Tsujimura, T., Sugihara, A., Takanashi, T., Uematsu, K., Terada, N., and Okamoto, E. The role of oval cells in rat hepatocyte transplantation. Transplantation 70(3), 441-446. 8-15-2000.
17. Kawakami, S., Munakata, C., Fumoto, S., Yamashita, F., and Hashida, M. Novel galactosylated liposomes for hepatocyte-selective targeting of lipophilic drugs. J. Pharm. Sci. 90(2), 105-113. 2001.
18. Hay, W. W., Jr. and Meznarich, H. K. Use of fetal streptozotocin injection to determine the role of normal levels of fetal insulin in regulating uteroplacental and umbilical glucose exchange. Pediatr. Res. 24(3), 312-317. 1988.
19. Yazova, A. K., Goussev, A. I., Poltoranina, V. S., and Yakimenko, E. F. Human alpha-fetoprotein epitopes as revealed by monoclonal antibodies. Immunol. Lett. 25(4), 325-330. 1990.
20. Jiang, Y., Jahagirdar, B. N., Reinhardt, R. L., Schwartz, R. E., Keene, C. D., Ortiz-Gonzalez, X. R., Reyes, M., Lenvik, T., Lund, T., Blackstad, M., Du, J., Aldrich, S., Lisberg, A., Low, W. C., Largaespada, D. A., and Verfaillie, C. M. Pluripotency of mesenchymal stem cells derived from adult Krause, D. S. Plasticity of marrow-derived stem cells. Gene Ther. 9: 754-758. 2002.
21. Ladiges et al, Lab. Anim. Sci. 40:11-15, 1990.
22. Henry et al. Am. J. Vet. Res. 46: 1714-20, 1985.
23. Civin, C. I. and Small, D. Purification and expansion of human hematopoietic stem/progenitor cells. Ann. N.Y. Acad. Sci. 770, 91-98. 1995.
24. Fujio, K., Evarts, R. P., Hu, Z., Marsden, E. R., and Thorgeirsson, S. S. Expression of stem cell factor and its receptor, c-kit, during liver regeneration from putative stem cells in adult rat. Lab. Invest. 70(4), 511-516. 1994.
25. Markakis, E. A. and Gage, F. H. Adult-generated neurons in the dentate gyrus send axonal projections to field CA3 and are surrounded by synaptic vesicles. J. Comp Neurol. 406(4), 449-460. 4-19-1999.
26. Stout, J. G. and Kirley, T. L. Control of cell membrane ecto-ATPase by oligomerization state: intermolecular cross-linking modulates ATPase activity. Biochemistry 35, 8289-8298. 1996.
27. Moore, R. A., Nguyen, Galceran, Pessah, N., and Allen, D. A transgenic myogenic cell line lacking ryanodine receptor protein for homologous expression studies: reconstitution of Ry1R protein and function. J. Cell Biol. 140(4), 843-851. 1998.
28. Wobus, A. M., Kaomei, G., Shan, J., Wellner, M. C., Rohwedel, J., Ji Guanju, Fleischmann, B., Katus, H. A., Hescheler, J., and Franz, W. M. Retinoic acid accelerates embryonic stem cell-derived cardiac differentiation and enhances development of ventricular cardiomyocytes. J. Mol. Cell Cardiol. 29(6), 1525-1539. 1997.
29. Cowan, P. J., Tsang, D., Pedic, C. M., Abbott, L. R., Shinkel, T. A., d'Apice, A. J., and Pearse, M. J. The human ICAM-2 promoter is endothelial cell-specific in vitro and in vivo and contains critical Sp1 and GATA binding sites. J. Biol. Chem. 273, 11737-11744. 1998.
30. Thompson, C. H., Jones, S. L., Whitehead, R. H., and McKenzie, I. F. A human breast tissue-associated antigen detected by a monoclonal antibody. J. Natl. Cancer Inst. 70(3), 409-419. 1983.
31. Brittan, M. and Wright, N. A. Gastrointestinal stem cells. J. Pathol. 197(4), 492-509. 2002.
32. Cabot, R. A., Kuhholzer, B., Chan, A. W., Lai, L., Park, K. W., Chong, K. Y., Schatten, G., Murphy, C. N., Abeydeera, L. R., Day, B. N., and Prather, R. S. Transgenic pigs produced using in vitro matured oocytes infected with a retroviral vector. Anim Biotechnol. 12(2), 205-214. 2001.
33. Chan, A. W. S., Homan, E. J., Ballou, L. U., Burns, J. C., and Bremel, R. D. Transgenic cattle produced by reverse transcribed gene transfer in oocytes. Proc. Natl. Acad. Sci. USA. 95:14028-3, 1998.
34. Ellison, A. R., Wallace, H., Al-Shawi, R., and Bishop, J. O. Different transmission rates of herpesvirus thymidine kinase reporter transgenes from founder male parents and male parents of subsequent generations. Mol. Reprod. Dev. 41, 425-434. 1995.
35. Gonzalez-Rothi, R. J., Suarez, S., Hochhaus, G., Schreier, H., Lukyanov, A., Derendorf, H., and Costa, T. D. Pulmonary targeting of liposomal triamcinolone acetonide phosphate. Pharm. Res. 13, 1699-1703. 1996.
36. Civin, C. I. and Small, D. Purification and expansion of human hematopoietic stem/progenitor cells. Ann. N.Y. Acad. Sci. 770, 91-98. 1995.
37. Fujio, K., Evarts, R. P., Hu, Z., Marsden, E. R., and Thorgeirsson, S. S. Expression of stem cell factor and its receptor, c-kit, during liver regeneration from putative stem cells in adult rat. Lab. Invest. 70(4), 511-516. 1994.
38. Hay, W. W., Jr. and Meznarich, H. K. Use of fetal streptozotocin injection to determine the role of normal levels of fetal insulin in regulating uteroplacental and umbilical glucose exchange. Pediatr. Res. 24(3), 312-317. 1988.
39. Yazova, A. K., Goussev, A. I., Poltoranina, V. S., and Yakimenko, E. F. Human alpha-fetoprotein epitopes as revealed by monoclonal antibodies. Immunol. Lett. 25(4), 325-330. 1990.
40. Hay, W. W., Jr. and Meznarich, H. K. Use of fetal streptozotocin injection to determine the role of normal levels of fetal insulin in regulating uteroplacental and umbilical glucose exchange. Pediatr. Res. 24(3), 312-317. 1988.
41. Yazova, A. K., Goussev, A. I., Poltoranina, V. S., and Yakimenko, E. F. Human alpha-fetoprotein epitopes as revealed by monoclonal antibodies. Immunol. Lett. 25(4), 325-330. 1990.

The invention claimed is:

1. A method of engrafting foreign replacement cells within a fetal non-human mammal, comprising the steps of:
   (a) selectively destroying native cells in a tissue of a fetal non-human mammal host, wherein the number of maternal cells of the same tissue is not substantially reduced; and thereafter
   (b) implanting foreign replacement cells in the tissue of the fetal non-human mammal host, whereby the foreign replacement cells replace destroyed cells of the tissue.

2. The method of claim 1 wherein the native cells of the tissue express a suicide gene product.

3. The method of claim 2 wherein the suicide gene product is selected from the group consisting of thymidine kinase, mutated thymidine kinase, cytosine deaminase, carboxylesterase, carboxypeptidase, deoxycytidine kinase, guanosine-xanthine phosphoribosyl transferase, nitroreductase, purine nucleoside phosphorylase, and thymidine phosphorylase.

4. The method of claim 1 wherein the tissue is selected from the group consisting of endothelium, hematopoietic cells, neural cells, epithelium, retinal pigment epithelium, myocardium, skeletal muscle, smooth muscle, progenitor cells, stem cells, lung, intestine, kidney, endocrine tissue, cartilage, and bone.

5. The method of claim 1 wherein the fetal non-human mammal is selected from the group consisting of a primate, an artiodactyl, a rodent, a carnivore, and a lagomorph.

6. The method of claim 1 wherein the foreign replacement cells are derived from the same species as the fetal non-human mammal host.

7. The method of claim 1 wherein the foreign replacement cells are derived from a different species than the fetal non-human mammal host.

8. The method of claim 1 wherein the foreign replacement cells are human cells.

9. The method of claim 1 wherein the native cells are destroyed using an immunoliposome.

10. The method of claim 1 wherein the native cells are destroyed using a liposome comprising a toxin or a prodrug.

11. The method of claim 10 wherein the liposome comprises a tissue-specific targeting ligand.

12. The method of claim 11 wherein the tissue-specific targeting ligand is an antibody.

13. The method of claim 1 wherein the tissue is liver.

14. The method of claim 1 wherein the fetal non-human mammal is an artiodactyl.

15. The method of claim 13 wherein the artiodactyl is a pig.

16. The method of claim 1 wherein the fetal non-human mammal host is a transgenic artiodactyl.

17. The method of claim 1 wherein the maternal cells are not transgenic.

18. A method of engrafting human replacement cells within a fetal pig, comprising the steps of:
   (a) selectively destroying native cells in a tissue of a fetal pig, wherein the number of maternal cells of the same tissue is not substantially reduced; and thereafter
   (b) implanting human replacement cells in the tissue of the fetal pig, whereby the human replacement cells replace destroyed cells of the tissue.

19. The method of claim 18 wherein the fetal pig is a transgenlc pig which expresses a suicide gene product.

20. The method of claim 18 wherein the tissue is selected from the group consisting of liver, endothelium, hematopoietic cells, neural cells, epithelium, retinal pigment epithelium, myocardium, skeletal muscle, smooth muscle, progenitor cells, stem cells, lung, intestine, kidney, endocrine tissue, cartilage, and bone.

21. The method of claim 19 wherein the suicide gene product is selected from the group consisting of thymidine kinase, mutated thymidine kinase, cytosine deaminase, carboxylesterase, carboxypeptidase, deoxycytidine kinase, guanosine-xanthine phosphoribosyl transferase, nitroreductase, purine nucleoside phosphorylase, and thymidine phosphorylase.

22. The method of claim 18 wherein the maternal cells are not transgenic.

* * * * *